(12) United States Patent
Baru Fassio (10) Patent No.: US 6,996,435 B2
(45) Date of Patent: Feb. 7, 2006

(54) IMPLANTABLE SIGNAL AMPLIFYING CIRCUIT FOR ELECTRONEUROGRAPHIC RECORDING

(75) Inventor: Marcelo Daniel Baru Fassio, Burnaby (CA)

(73) Assignee: Neurostream Technologies Inc., (CA)

( * ) Notice: Subject to any disclaimer, the term of this patent is extended or adjusted under 35 U.S.C. 154(b) by 72 days.

(21) Appl. No.: 09/988,112

(22) Filed: Nov. 19, 2001

(65) Prior Publication Data

US 2003/0097050 A1 May 22, 2003

(51) Int. Cl.
*A61B 5/00* (2006.01)

(52) U.S. Cl. .................................. 600/544
(58) Field of Classification Search ............. None
See application file for complete search history.

(56) References Cited

U.S. PATENT DOCUMENTS

| | | | |
|---|---|---|---|
| 3,927,377 A | 12/1975 | Iwazumi | |
| 4,750,499 A | 6/1988 | Hoffer | |
| 5,111,815 A * | 5/1992 | Mower | 607/4 |
| 5,339,285 A | 8/1994 | Straw | |
| 5,358,514 A * | 10/1994 | Schulman et al. | 607/61 |
| 5,861,778 A | 1/1999 | Louagie et al. | |
| 6,587,725 B1 * | 7/2003 | Durand et al. | 607/42 |

OTHER PUBLICATIONS

J. A. Hoffer and K. Kallesøe, "How to Use Nerve Cuffs to Stimulate, Record or Modulate Neural Activity", Neural Prostheses for Restoration of Sensory and Motor Function, Chapter 5, CRC Press, 2000.

K. Papathanasiou and T. Lehmann, "An Implantable CMOS Signal Conditioning System for Recording Nerve Signals with Cuff Electrodes", *Proceedings of the IEEE International Symposium on Circuits and Systems*, pp. V 281-284, Switzerland, May 2000.

T. Sinkjær et al., "Electroneurographic (ENG) Signals from Intradural S3 Dorsal Sacral Nerve Roots in a Patient with SupraSacral Spinal Cord Injury", *Proceedings of the 5th Annual Conference of the International Function Electrical Stimulation Society*, pp. 361-364, Denmark, Jun. 2000.

N. Donaldson et al., "An Implantable Telemeter for Long-Term Electroneurographic Recordings in Animals and Humans", *Proceedings of the 5th Annual Conference of the International Function Electrical Stimulation Society*, pp. 378-381, Denmark, Jun. 2000.

K.D. Strange and J.A. Hoffer, "Gait Phase Information Provided by Sensory Nerve Activity During Walking: Applicability as State Controller Feedback for FES", *IEEE Transactions on Biomedical Engineering*, vol. 46, No. 7, pp. 797-809, Jul. 1999.

(Continued)

Primary Examiner—Robert L. Nasser
(74) Attorney, Agent, or Firm—Seyfarth Shaw LLP; Timothy J. Keefer (57) ABSTRACT

An implantable microvolt-level signal amplifying circuit may be used for resolving electrical signals generated by nerves in the presence of larger amplitude signals generated by muscles, the heart, or external noise sources. The circuit has a low-noise, high Common Mode Rejection Ratio (CMRR) preamplifier, followed by a cascade of stages, which provide filtering and further amplification of the neural signal. The band-pass amplifying circuit can also present high Power Supply Rejection Ratio (PSRR). The output is offset-compensated by a DC restoration stage. Nerve protection circuitry minimizes or blocks DC current flow through the input terminals in the event of semiconductor failure in the preamplifier. The circuit may be incorporated onto a common monolithic circuit with follow-up circuitry for controlling Functional Electrical Stimulation (FES) devices.

17 Claims, 4 Drawing Sheets

OTHER PUBLICATIONS

D.M. Binkley et al., "A Micropower CMOS, Direct-Conversion, VLF Receiver Chip for Magnetic-Field Wireless Applications", *IEEE Journal of Solid-State Circuits*, vol. 33, No. 3, pp. 344-358, Mar. 1998.

F. Silveira, D. Flandre and P. Jespers, "A $gm/I_D$ Based Methodology for the Design of CMOS Analog Circuits and Its Application to the Synthesis of a Silicon-On-Insulator Micropower OTA", *IEEE Journal of Solid-State Circuits*, vol. 31, No. 9, pp. 1314-1319, Sep. 1996.

C. C. Enz et al., "An Analytical MOS Transistor Model Valid in All Regions of Operation and Dedicated to Low-Voltage and Low-Power Applications", *Analog Integrated Circuits and Signal Processing*, No. 8, pp. 83-114, 1995.

Z.M. Nikolić et al., "Instrumentation for ENG and EMG Recordings in FES Systems", *IEEE Transactions on Biomedical Engineering*, vol. 41, No. 7, pp. 703-706, Jul. 1994.

M.K. Haugland and J.A. Hoffer, "Slip Information Provided by Nerve Cuff Signals: Application in Closed-Loop Control of Functional Electrical Stimulation", *IEEE Transactions on Rehabilitation Engineering*, vol. 2, No. 1, pp. 29-36, Mar. 1994.

A.R. Alvarez, "BiCMOS Technology and Applications", Second Edition, Kluwer Academics Publishers, 1993.

E.A. Vittoz, "Micropower Techniques, Design of VLSI Circuits for Telecommunications and Signal Processing", Eds. J.E. Franca and Y.P. Tsividis, Prentice Hall, 1993.

G. Nicollini and C. Guiardiani, "A 3.3-V 800-$nV_{rms}$ Noise, Gain-Programmable CMOS Microphone Preamplifier Design Using Yield Modeling Technique", *IEEE Journal of Solid-State Circuits*, vol. 28, No. 8, pp. 915-921, Aug. 1993.

E. Säckinger et al., "A General Relationship Between Amplifier Parameters, and Its Application to PSRR Improvement", *IEEE Transactions on Circuits and Systems*, vol. 38, No. 10, Oct. 1991.

E. Säckinger and W. Guggenbühl, "A Versatile Building Block: The CMOS Differential Amplifier", *IEEE Journal of Solid-State Circuits*, vol. 22, No. 2, pp. 287-294, Apr. 1987.

R. Gregorian and G.C. Temes, "Analog MOS Integrated Circuits for Signal Processing", John Wiley & Sons, 1986.

R.P. Jindal, "Noise Associated with Distributed Resistance of MOSFET Gate Structures in Integrated Circuits", *IEEE Transactions on Electron Devices*, vol. ed-31, No. 10, pp. 1505-1509, Oct. 1984.

P.R. Gray and R.G. Meyer, "MOS Operational Amplifiers Design—a Tutorial Overview", *IEEE Journal of Solid-State Circuits*, vol. sc-17, No. 6, pp. 969-982, Dec. 1982.

Kim, K.H and S.J. Kim, "Noise Characteristic Design of CMOS Source Follower and Voltage Amplifier for Active Semiconductor Microelectrodes for Neural Signal Recording," *Medical & Biological Engineering & Computing 38*: 469-472, 2000.

* cited by examiner

IMPLANTABLE SIGNAL AMPLIFYING CIRCUIT FOR ELECTRONEUROGRAPHIC RECORDING

TECHNICAL FIELD

This invention is related to the amplification of neural signals recorded using nerve cuff electrodes or other implantable nerve electrodes. In particular, it relates to an implantable amplifying circuit. Specific embodiments of the invention provide gain and filtering and can serve as a front-end amplifier between nerve cuff electrodes and follow-on implanted circuitry.

BACKGROUND

As shown by K. D. Strange and J. A. Hoffer, "*Gait Phase Information Provided by Sensory Nerve Activity During Walking: Applicability as State Controller Feedback for FES*", IEEE Transactions on Biomedical Engineering, vol. 46, no. 7, pp. 797–809, July 1999, the natural sensory signals recorded by nerve cuff electrodes can be used as a reliable source of feedback for closed-loop control of Functional Electrical Stimulation (FES) devices. As other examples, bladder pressure can be measured to control micturition, or sensory feedback from touch sensors in the skin can be recorded for improved activation of paralyzed limb muscles; see, for example, T. Sinkjaer et. al., "*Electroneurographic (ENG) Signals from Intradural S3 Dorsal Sacral Nerve Roots in a Patient with SupraSacral Spinal Cord Injury*", Proceedings of the 5$^{th}$ Annual Conference of the International Functional Electrical Stimulation Society, pp. 361–364, Denmark, June 2000; and M. K. Haugland and J. A. Hoffer, "*Slip Information Provided by Nerve Cuff Signals: Application in Closed-Loop Control of Functional Electrical Stimulation*", IEEE Transactions on Rehabilitation Engineering, vol. 2, no. 1, pp. 29–36, March 1994, respectively.

Recording nerve cuff electrodes were introduced as a research tool in the 1970's and the first human trials started in the 1990's. See J. A. Hoffer and K. Kallesøe, "*How to Use Nerve Cuffs to Stimulate, Record or Modulate Neural Activity*", Neural Prostheses for Restoration of Sensory and Motor Function, Chapter 5, CRC Press, 2000.

Several different nerve signals are needed to control a prosthetic device; see U.S. Pat. No. 4,750,499 to Hoffer for a "*Closed-Loop, Implanted-Sensor, Functional Electrical Stimulation System for Partial Restoration of Motor Functions*". The signals picked up by the nerve cuff electrodes have been recorded mainly using commercially available components located externally to the body, which consume a lot of area and a lot of power. Such recording setups require long leads that course transcutaneously. This increases the risk of infection for the patient. Long cables also increase the risk of wire breakage and reduce portability. The added resistance and capacitance of long cables can contribute to signal shunting and greater pick-up of unwanted signals (e.g. stimulation artifacts and power-line influx noise).

The biggest problems in recording neural signals using nerve cuff electrodes are the very low signal amplitude and low signal-to-noise ratio (S/N) that are characteristic of these signal sources. When dealing with signals in the $\mu V$ range, minimization of the preamplifier noise is of extreme importance. Under such conditions, it is useful to passively boost the signal amplitude with an audio transformer before it encounters the first active amplification stage. This has been a common practice in recording neural signals. See, for example, Z. M. Nikolić et. al., "*Instrumentation for ENG and EMG Recordings in FES Systems*", IEEE Transactions on Biomedical Engineering, vol. 41, no. 7, pp. 703–706, July 1994. The smallest audio transformers in the market have an area of around 1 cm$^2$. Since several transformers would be needed in a multi-channel recording device, this solution is impractical.

Recently, N. Donaldson et al. described an implantable, single-channel cuff-recording system, fabricated using discrete components, which uses no input transformer. See N. Donaldson et al., "*An Implantable Telemeter for Long-Term Electroneurographic Recordings in Animals and Humans*", Proceedings of the 5$^{th}$ Annual Conference of the International Functional Electrical Stimulation Society, pp. 378–381, Denmark, June 2000. This design, although useful for research purposes, has limitations in its clinical applicability due to its size and power requirements, and is not suitable for clinical applications where several recording-channels are needed.

Various designs of custom-integrated amplifiers for neural activity recording have been presented throughout the years. However, these designs have generally dealt with neural source voltage amplitudes at least two orders of magnitude larger than the signals that are typically recorded using nerve cuff electrodes.

K. Papathanasiou and T. Lehmann, "*An Implantable CMOS Signal Conditioning System for Recording Nerve Signals with Cuff Electrodes*", Proceedings of the IEEE International Symposium on Circuits and Systems, pp. V 281–284, Switzerland, May 2000 discloses an integrated amplifier. There is no mention of noise levels and the amplifier gain is of the open-loop type. Open-loop amplifiers present several problems associated with their high gain. Two of the main problems are potential saturation due to intrinsic amplifier offset and muscular activity (EMG) of much higher amplitude than the nerve signals of interest, requiring the amplifier to utilize special circuit techniques to compensate for these effects. Furthermore, FES systems based on closed-loop feedback control typically require amplifiers having variable gain.

There is a need for an amplifying circuit that is suitable for use in implantable devices. There is a particular need for such a circuit which can provide several externally controllable gain levels, as required for the development of FES systems based on closed-loop feedback control.

SUMMARY OF THE INVENTION

This invention provides a low-noise signal band-pass amplifying circuit for ENG recording using nerve cuff electrodes or other implantable nerve electrodes. The circuit may be used in implantable devices. The devices may be implanted in close proximity to a nerve cuff electrode or other electrode which detects a bioelectrical signal. The band-pass amplifying circuit provides the gain and filtering in order to serve as the front-end amplifier between a nerve cuff electrode and the follow-on implanted circuitry. A circuit according to the invention may be incorporated on a common monolithic integrated circuit with follow-on circuitry.

In preferred embodiments, the band-pass amplifying circuit is small in area and has low power consumption. This makes the circuit suitable for clinical applications where multi-channel recording is needed. The band-pass amplifying circuit may be constructed in a single monolithic integrated circuit without the need of any external components.

In preferred embodiments, the gain is selectable and can easily be changed using switches that select different combinations of resistor ratios. The variable gain may be used in FES systems based on closed loop feedback control to accommodate different ENG recording ranges (for example, natural sensory traffic information and compound-action-potentials elicited by electrical stimulation) into the same output voltage range. The output signal may be digitized using implanted circuitry. The band-pass amplifying circuit has high CMRR, when used with nerve cuff electrodes, high PSRR, and is stable in the presence of stimulus artifacts elicited nearby by electrical stimulation.

Preferred embodiments provide a system in which a signals, picked up by a nerve cuff electrode, passed through nerve protection circuitry, and then amplified by a low-noise, high-CMRR, high-PSRR preamplifier. The amplified signal may be further band-pass filtered using two cascades of high-PSRR, first order band-pass amplifiers. The output is preferably offset-compensated by a DC restoration stage where the stage following the band-pass amplifying circuit is nonlinear. The band-pass amplifying circuit may be fully integrated.

The amplifying circuit can, for example, be powered by an RF telemetry link. It can also be powered by a battery or other known means for supplying electrical energy.

The general specifications which it is desirable that an implantable band-pass amplifying circuit possess for ENG recording using nerve cuff electrodes can be summarized as follows:

The filtering shall be second order or higher. The pass frequency range shall preferably be between approximately 900 Hz and 9 kHz, for 5 $\mu V_{peak}$ input neural signals.

The equivalent input noise at 3 kHz shall preferably be lower than 0.6 $\mu V_{rms}$.

The CMRR at 250 Hz shall preferably be higher than 90 dB.

The power consumption shall preferably be lower than 12 mW.

If the implantable device is going to be powered by an RF telemetry link, then the PSRR of the band-pass amplifying circuit at 3 kHz shall preferably be higher than 85 dB.

Preferred embodiments of the invention meet these specifications.

BRIEF DESCRIPTION OF DRAWINGS

In Figures which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
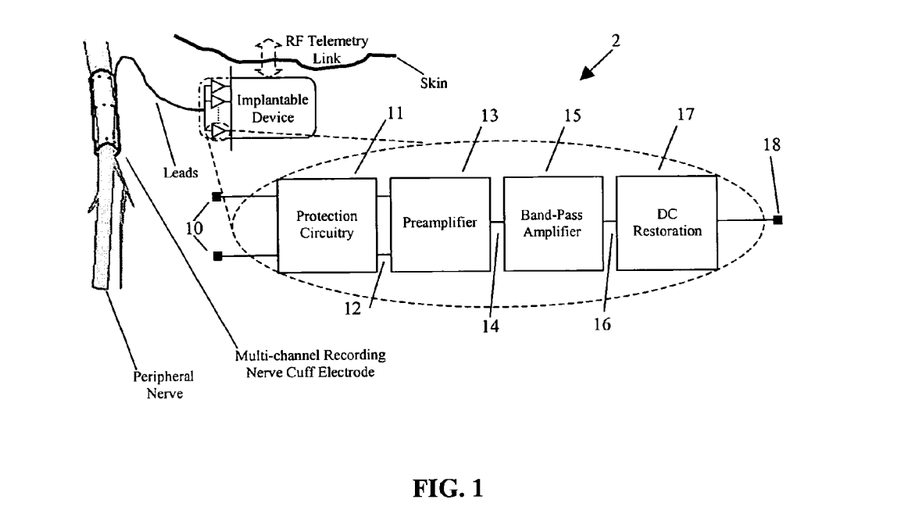
FIG. 1 is a block diagram of the band-pass amplifying circuit according to the invention.

FIG. 1 is a block diagram of the band-pass amplifying circuit 2 according to an embodiment of the invention. Circuit 2 has input terminals 10 connected to receive a signal. The signal is typically a bioelectrical signal such as a signal picked up by a nerve cuff electrode or other implantable nerve electrode. The signal is coupled from input terminals 10 through protection circuitry 11, which in turn passes the signal to inputs 12 of preamplifier stage 13. The preamplified signal at the output 14 of preamplifier 13 is fed into a band-pass amplifier 15, whose output 16 is fed into a DC restoration stage 17. Circuit 2 provides an output signal at point 18. The output signal may be provided to follow-on circuitry or devices.

In an implantable application, it is imperative to minimize any DC current flow through the electrodes to avoid electrolysis, or in the case of a semiconductor failure, to protect a subject's nerves from irreversible damage. Protection circuitry 11 has the function of blocking or at least minimizing any DC current flow through input terminal 10 (and any implanted electrode connected to input terminal 10). If a malfunction, such as a semiconductor failure, in preamplifier 13 permits current to flow at the input of preamplifier 13 then protection circuitry 11 prevents the flow of current in an amount which would harm the subject's nerves.

Current regulations and good design practice suggests that a subject have at least two stages of protection to prevent excessive currents at input terminals 10. Preamplifier 13 could be designed with a bipolar input stage. Protection circuit 11 could then be designed to provide two or more protection stages. Bipolar transistors require large input bias currents for their operation. The bias current may be hundreds of nA. Good design, and applicable regulations both require that no single component failure should be able to cause significant currents to flow in input terminals 10. The protection stages of protection circuit 11 typically are implemented using discrete components, due to the time constants involved. Such discrete components occupy a large area.

The circuits according to the preferred embodiments of this invention use a CMOS input stage in preamplifier 13. Since the input bias current of a CMOS transistor is in the order of fA, only one additional protection stage is needed. The input stage of preamplifier 13 itself acts as a protection stage. This permits protection circuitry 11 to be reduced to a single high-value resistor in parallel with a capacitor which is preferably implemented as a series of two capacitors as shown for example in FIG. 2b. This, in turn, reduces the overall size of circuit 2.

As mentioned above, the noise of the band-pass amplifying circuit 2 is dictated primarily by the input stage of preamplifier 13.

Preamplifier 13 is preferably implemented as a differential difference amplifier (DDA). A DDA by G. Nicollini and C. Guardiani, "A 3.3-V 800-$nV_{rms}$ Noise, Gain-Programmable CMOS Microphone Preamplifier Design Using Yield Modeling Technique", IEEE Journal of Solid-State Circuits, vol. 28, no. 8, pp. 915–921, August 1993. The basic DDA architecture was introduced by E. Säckinger and W.

Guggenbühl, "*A Versatile Building Block: The CMOS Differential Difference Amplifier*", IEEE Journal of Solid-State Circuits, vol. 22, no. 2, pp. 287–294, April 1987. Several circuits custom-designed for different applications, based on this structure, have been patented. See, for example, U.S. Pat. No. 5,861,778 to Louagie et al. for a "Low Noise Amplifier Structure" and U.S. Pat. No. 5,339,285 to Straw for a "Monolithic Low Noise Preamplifier for Piezoelectric Sensors".

Band-pass amplifier 15 may be implemented by cascading two high-PSRR, first-order band-pass amplifiers, each one composed of a $g_m$-C high-pass filter and a low-pass amplifying circuit. DC restoration stage 17 can also be implemented using a $g_{mo}$-$C_o$ high-pass filter, but with a input-linear-range higher than the input linear ranges of the high-pass filters of band-pass amplifier 15.

Figure 2A:
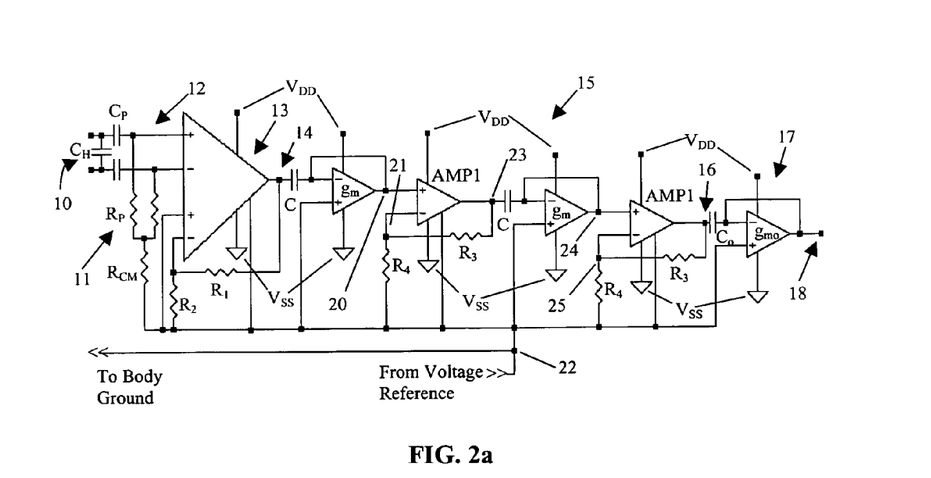
FIGS. 2a and 2b are circuit diagrams showing two alternative architectures for the band-pass amplifying circuit.
Figure 2B:
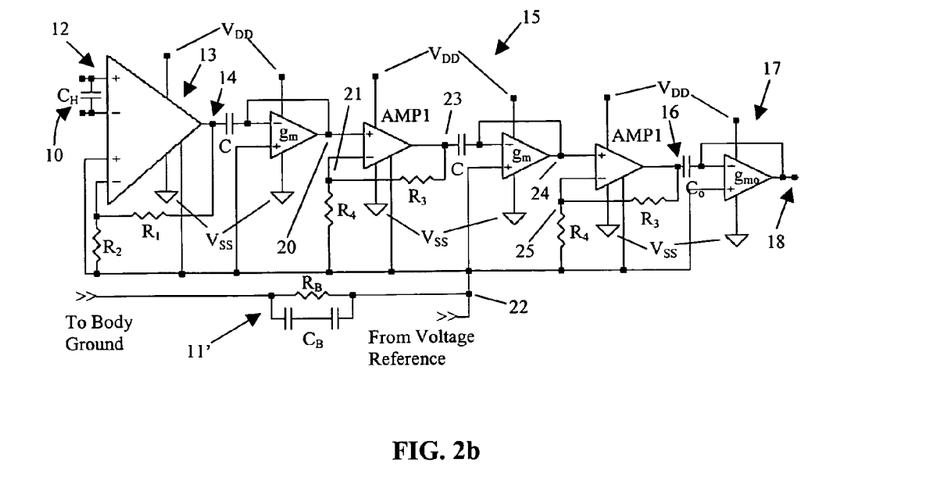

Two alternative architectures for the circuit presented in this invention are shown in FIGS. 2a and 2b. In FIG. 2a, protection circuitry 11 comprises a discrete $R_p$-$C_p$ high-pass filter that blocks completely any DC current flow caused by a semiconductor failure in preamplifier 13. Resistor $R_{CM}$ causes protection circuitry 11 to act in the same way on both input terminals 10. This avoids degradation of the CMRR due to the presence of protection circuitry 11.

Alternatively, in FIG. 2b, protection circuitry 11' comprises a high-value resistor $R_B$ in parallel with a series of capacitors $C_B$. Protection circuitry 11' minimizes any DC current flow caused by a semiconductor failure in preamplifier 13. Capacitors $C_B$ are selected to minimize power-line noise. In terms of noise performance and number of external components needed, the protection circuit 11' in FIG. 2b is preferable to the protection circuit 11 of FIG. 2a. However, in case of a semiconductor failure, protection circuit 11 completely blocks any DC flow to the electrodes and tissues as opposed to reducing the DC flow below an acceptable threshold.

In preferred embodiments, band-pass amplifier 2 has a single-ended output architecture. While a differential output can be used in the context of the invention and may provide enhanced performance, significant area and power penalties must be paid to achieve those benefits.

Gain programmability may be achieved, as shown in FIGS. 2a and 2b, by using switches that select different combinations of resistors to vary the ratios of R3 to R4. The gain of preamplifier 13, in the recording band, may be fixed and given by the ratio (1+R1/R2). In preferred embodiments, the high-pass filtering stages are implemented with $g_m$-C filters since precision in the poles is not crucial. The closed-loop transfer function of the low-pass amplifier AMP1 may be set to have its dominant pole at 9 kHz (for 5 $\mu V_{peak}$ input neural signals), while providing the necessary further gain. Such DC gain is given by the ratio (1+R3/R4). The DC restoration stage 17 may comprise a $g_{mo}$-$C_o$ high-pass filter, preferably with an input linear range higher than 0.2 V. Precision again is not crucial since this stage is only needed for compensation of the band-pass amplifying circuit offset. Finally, in FIGS. 2a and 2b it can be observed that a reference voltage 22 is supplied as an input to the preamplifier 13 and the two low-pass amplifiers AMP1. This contributes to improving the PSRR of the band-pass amplifying circuit in the recording band, as explained below.

Figure 3:
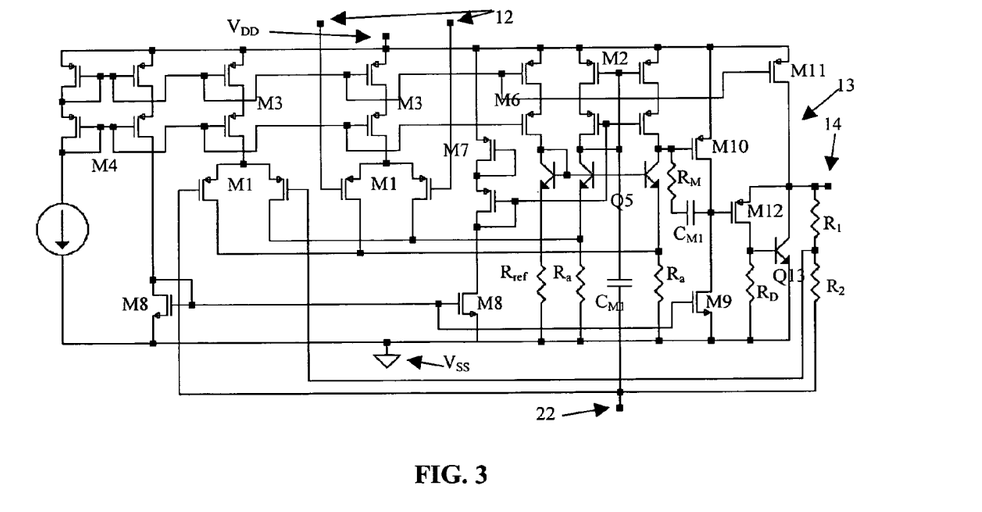
FIG. 3 is a circuit diagram for the preamplifier circuit based on a "Differential Difference Amplifier" (DDA)

FIG. 3 shows a possible circuit for preamplifier 13. The M1 differential pairs realize the transconductance elements of a two-stage DDA. The current sources M3 are implemented using a cascode design as described in R. Gregorian and G. C. Temes, "*Analog MOS Integrated Circuits for Signal Processing*", pp. 131–133, John Wiley & Sons, 1986. This provides good matching of the two input stages, which is important in optimizing the performance of a DDA. On the other hand, the use of cascode current sources adds a PMOS threshold voltage $V_T$ to the minimum supply voltage $V_{DD}$ needed for operation; however, in this case the supply voltage $V_{DD}$ is typically not a limiting factor.

The differential current generated by transistors M1 is converted into a single-ended current by a cascode configuration, comprising transistors Q5 and cascode mirror M2. With this configuration, better frequency response can be achieved than in the case of an amplifier based on a cascade of two common-source stages. This is particularly true in the case of preamplifier 13, since the parasitic capacitance given by the large input transistors M1 (needed to achieve low-noise) is considerable. Transistor M10 provides further gain and accommodates the biasing of the output stage composed by M11, M12, Q13 and $R_D$. The second stage of preamplifier 13 could comprise a single transistor but, in the preferred embodiment, comprises a transistor M10 with capacitors $C_{M1}$ and $R_M$ providing frequency compensation. See P. R. Gray and R. G. Meyer, "*MOS Operational Amplifiers Design—a Tutorial Overview*", IEEE Journal of Solid-State Circuits, vol. sc-17, no. 6, pp. 969–982, December 1982.

Finally, the equivalent Darlington pnp transistor M12-Q13 provides very low output impedance while drawing no current from the second stage. See A. R. Alvarez, "*BiCMOS Technology and Applications*", pp. 317–318, Second Edition, Kluwer Academics Publishers, 1993. In this way, preamplifier 13 provides negligible systematic offset independent of variations in the electrical characteristics of the fabrication process. This is important for the successful performance of a DDA.

The transistors may be sized according to the methods presented by F. Silveira, D. Flandre and P. Jespers, "*A gm/$I_D$ Based Methodology for the Design of CMOS Analog Circuits and Its Application to the Synthesis of a Silicon-On-Insulator Micropower OTA*", IEEE Jounal of Solid-State Circuits, vol. 31, no. 9, pp. 1314–1319, September 1996. These methods are based on the relation of the transconductance over drain current ratio ($g_m/I_D$), to the normalized current ($I_D/(W/L)$) and allow a unified treatment of all regions of operation of the MOSFET transistors. Sizing of the transistors can be achieved for example by using this method and the EKV model, with a set of parameters and measurements from the process. See E. A. Vittoz, "*Micropower Techniques, Design of Analog-Digital VLSI Circuits for Telecommunications and Signal Processing*", pp. 53–67, Eds. J. E. Franca and Y. P. Tsividis, Prentice Hall, 1993; and C. C. Enz et al., "*An Analytical MOS Transistor Model Valid in All Regions of Operation and Dedicated to Low-Voltage and Low-Power Applications*", Analog Integrated Circuits and Signal Processing, no. 8, pp. 83–114, 1995.

A main specification that applies to the preamplifier 13 is its noise level. The equivalent total input noise spectral density $S_i$ has the following expression:

$$S_i = 4S_{M1} + S_{R2} + 4\left(\frac{g_{M2}}{g_{M1}}\right)^2 S_{M2} + 2\left(\frac{1}{g_{M1}R_a}\right)^2 S_{Ra} + \frac{S_{1/gm}}{A_{cDDA}^2 (f/f_{HPF})^2} \quad (1)$$

The factors in equation (1) are as follows:

$S_{M1}$ represents the noise contribution of an M1 input transistor. There are four of these transistors contributing directly to the input noise. The noise of preamplifier 13 is dominated by this factor.

$S_{R2}$ represents the noise contribution of resistance R2 that passes directly to the inputs 12.

$S_{M2}$ represents the noise contribution of a M2 current mirror transistor. The contribution of these loads is reduced by the square of the ratio of their transconductance to that of the input transistors M1.

$S_{Ra}$ represents the noise contribution of a $R_a$ resistor. The contribution of these resistors is also reduced by the square of the product of their value and the transconductance of the input transistors M1.

$S_{1/gm}$ is the noise of the equivalent resistor of the $g_m$-C high-pass filter. $S_{1/gm}$ is reduced by two factors. First of all, it is reduced by the gain of the preamplifier 13 ($A_{cDDA}$), since this stage precedes the filter, and second it decreases with frequency as stated in equation (1). This decrease is logical since, after the high-pass filter pole ($f_{HPF}$), the capacitor C can be seen as a short circuit. This places the equivalent resistor $1/g_m$ in parallel with resistor R1.

A rough calculation shows that, in order to maintain a noise level from thermal sources which does not exceed approximately 0.6 $\mu V_{rms}$ in a 10 kHz bandwidth, the total equivalent input noise should be $\overline{S_1}$=6nV/$\sqrt{Hz}$. Since in a well-designed amplifier the input transistors dominate the noise, the required level of MOSFET transconductance can be achieved only near weak inversion. The selection of the MOSFET type for the input transistors M1 was studied in detail. It is well known that in strong inversion the flicker noise of a PMOS transistor is lower than that of NMOS transistors. However, it has been reported that flicker noise in PMOS transistors may significantly increase when such transistors move from strong inversion toward weak inversion. See D. M. Binkley et al., "A Micropower CMOS, Direct-Conversion, VLF Receiver Chip for Magnetic-Field Wireless Applications", IEEE Journal of Solid-State Circuits, vol. 33, no. 3, pp. 344–358, March 1998. Still others have reported the flicker noise going down, indicating that it arises from a mechanism that is strongly affected by details of device fabrication. The very severe increase in flicker noise has not been observed in prototype circuits according to this invention. Therefore transistors M1 may be PMOS in some embodiments of the invention. In embodiments in which the band-pass amplifying circuit 2 is fabricated using an N-well technology, this selection improves the PSRR of the circuit as well.

By implementing the transfer function of the band-pass amplifying circuit 2 and the noise equation given by equation (1) in the MATLAB® design environment, thermal noise levels for each factor were assigned. This approach led to a value of $(g_m/I_D)$=16.81V$^{-1}$ for the input transistors M1, that corresponds to a (W/L)=4480. Common-centroid crossed-coupling layouts may be used for transistors M1. R. P. Jindal, "Noise Associated with Distributed Resistance of MOSFET Gate Structures in Integrated Circuits", IEEE Transactions on Electron Devices, vol. ed-31, no. 10, pp. 1505–1509, October 1984 describes some common-centroid crossed-coupling layouts.

The load M2 in a prototype circuit according to the invention resulted deep in strong inversion because its transconductance was chosen almost five times lower than that of the input transistors to minimize noise. This resulted in a (W/L)=74.5.

Resistors $R_a$ were dimensioned based on biasing requirements, noise minimization, and the folded cascode requirement that $g_{M5} R_a \gg 1$. This integrated resistor is made of a p$^+$ diffusion, with a typical value in the range of 64 to 96 to $\Omega/\square$ (ohms per square). In the currently preferred embodiment, $R_a$ has a value of 2245 $\Omega$.

The CMRR of the embodiment of preamplifier 13 shown in FIG. 3 may be expressed by:

$$CMRR = \frac{1}{\frac{1}{2g_{M1}R_{oM3}} \frac{\Delta g_{M1}}{g_{M1}} + \frac{\Delta \mu_1}{\mu_1}} \quad (2)$$

where $R_{oM3}$ is the output impedance of the cascode current source formed by transistors M3, $\Delta g_{M1}$, is the mismatch between the transconductances of transistors M1, $\mu_1$ is the voltage gain of transistors M1, and $\Delta \mu_1$, is the mismatch between the voltage gains of such transistors. Based on mismatch measurements previously performed for the present technology, the size of transistor M4 may be chosen to be (W/L)=20.3. Transistor M3 is composed of a few transistors M4 in order to provide the necessary bias current level for the input transistors M1. In this way, the CMRR given by equation (2) is mainly determined by the mismatch in the voltage gain $\mu_1$. CMRRs in the order of 95 dB can be achieved.

The output stage formed by M11, M12, Q13 and $R_D$, may be designed based on the excursion expected at output 14. Amplified EMG signals caused by mismatches in nerve cuffs as well as random offset of the preamplifier 13 should be taken into account.

The design of the second stage composed by M9, M10, $C_{M1}$, and $R_M$ was based on the minimization of systematic offset and the phase margin desired for the preamplifier 13. In a prototype circuit according to the invention, transistors Q5-Q13 have an emitter area of 6.4×9.6 $\mu m^2$.

The connection of capacitor $C_{M1}$ between reference voltage 22 and the gate of one of the M2 transistors, as shown in FIG. 3, improves the PSRR of preamplifier 13. As analyzed by E. Säckinger et al., "A General Relationship Between Amplifier Parameters, and Its Application to PSRR Improvement", IEEE Transactions on Circuits and Systems, vol. 38, no. 10, pp. 1173–1181, October 1991, there is a constraint for the simultaneous improvement of the CMRR and the PSRR in any kind of amplifier. The PSRR of single-ended amplifiers can be improved and rejection in the mid-frequency range can be improved by connecting a capacitor between the amplifier input and a noise-free reference, in this case, reference voltage 22. This is the role capacitor $C_{M1}$ plays in the preamplifier 13.

Figure 4:
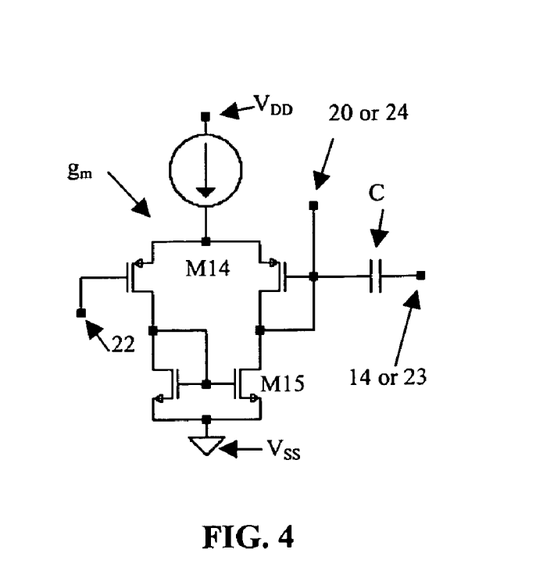
FIG. 4 is a circuit diagram for the high-pass filter circuit component of the band-pass amplifier.

As mentioned above, band-pass amplifier 15 may be implemented by cascading two high-PSRR, first-order band-pass amplifiers, each composed of a $g_m$-C high-pass filter and a low-pass amplifying circuit. In FIG. 4, the $g_m$-C high-pass filter is shown. The transconductance $g_m$ is provided by a basic differential pair with active load. All the transistors shown are placed in the moderate inversion region. This provides enough linear range for the present application.

Figure 5:
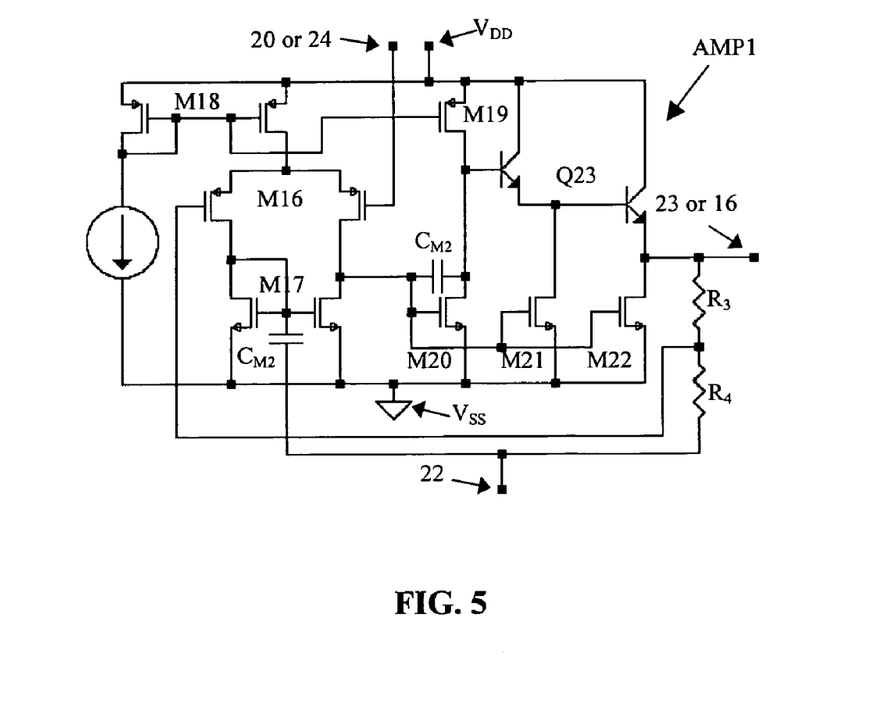
FIG. 5 is a circuit diagram for the low-pass amplifying circuit component of the band-pass amplifier.

FIG. 5 shows a preferred embodiment of the amplifier AMP1. This is a Miller-type amplifier with a Darlington output stage that provides low-output impedance. Darlington transistors Q23 obtain their bias currents from transistors M21 and M22, which also carry signal current, making the amplifier a class AB. This reduces power consumption since it avoids the need of extra transistors to bias transistors Q23.

Resistors $R_3$ and $R_4$ provide feedback for closed-loop operation. Since the two amplifiers AMP1 give the low-pass filter characteristic of the band-pass amplifying circuit 2, its cutoff frequency is set by the gain of this stage and by the high-pole specification of the band-pass amplifying circuit 2. Capacitor $C_{M2}$ connected between reference voltage 22 and the gates of transistors M17 increases the PSRR in the passed band, as explained above for the preamplifier 13.

Figure 6:
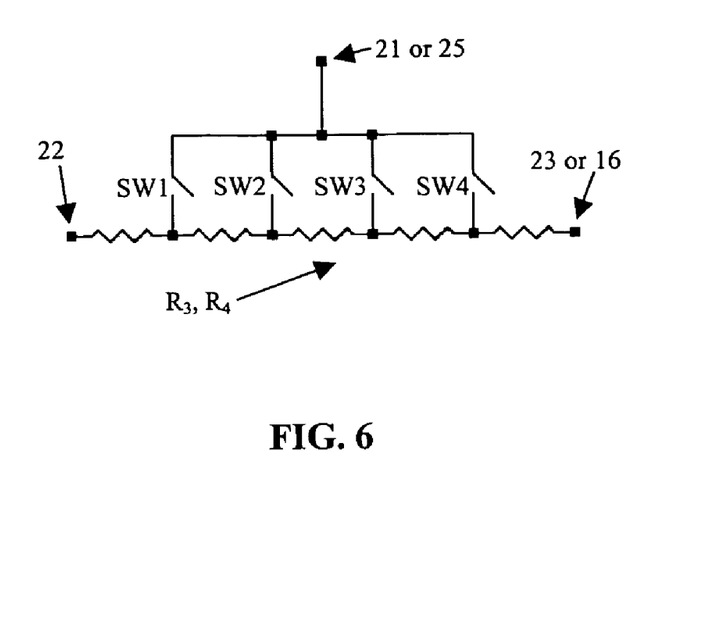
FIG. 6 is a circuit diagram showing a gain programmability obtained by an N-well resistor string and four switches selected one at a time according to the desired gain of the low-pass amplifying circuit of FIG. 5; and, FIG. 7 is a circuit diagram for the DC restoration stage.

FIG. 6 shows the gain programmability obtained by using an N-well resistor string and four switches SW1 to SW4 to select different combinations of resistors to vary the ratios of R3 to R4. Switches SW1 to SW4 may be electronic switches controlled by control logic (now shown). In this example, switches SW1 to SW4 are selected one at a time according to the desired gain for AMP1. The switches SW1 to SW4 are placed in series with the feedback inputs 21 and 25, and therefore their finite "on" resistance does not affect the gain. Of course, the number of switches and resistors can be varied depending on the number of externally controlled gain levels desired.

Figure 7:
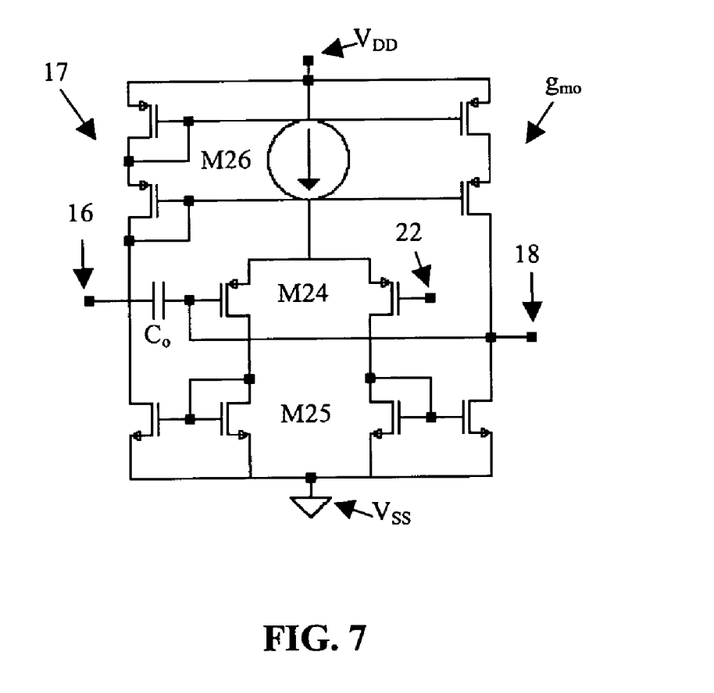

Finally, FIG. 7 shows the DC restoration stage. It is implemented using a $g_{mo}$-$C_o$ high-pass filter since precision in the pole is not critical. The cutoff frequency is preferably in the range of 400 Hz to 600 Hz and is most preferably about 480 Hz. This further helps to reduce noise of biological origin while allowing band-pass amplifying circuit 2 to recover within a few milliseconds from overload such as could be caused by stimulation currents or while being cycled on/off.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An implantable amplifying circuit for recording electrical signals generated by a nerve and detected by a pair of electrode wires in contact with the nerve, the amplifying circuit comprising:
   a preamplifier having a pair of inputs for receiving signals from the pair of electrode wires, the preamplifier including a differential pair of input MOSFET transistors having a low input current that serves as a first protection circuit to limit current flow through the nerve and the electrode wires, a pair of bipolar transistors and a current mirror that are driven with differential outputs of the MOSFET input transistors and producing a single-ended nerve output signal;
   a common signal line adapted to connect a body ground of a patient to a common voltage of the amplifying circuit;
   a second protection circuit disposed in series with the common signal line including a parallel resistor/capacitor combination to limit current flow through the nerve and the common signal line.

2. The implantable amplifying circuit of claim 1, wherein said second protection circuit comprises a resistor in parallel with a series of one or more capacitors.

3. The implantable amplifying circuit of claim 1, further comprising:
   at least one amplifier stage connected to the preamplifier single-ended nerve output signal that produces an amplified nerve output signal.

4. The implantable amplifying circuit of claim 1, wherein the implantable amplifying circuit has an equivalent input noise at 3 kHz that is lower than 0.6 $\mu V_{rms}$.

5. The implantable amplifying circuit of claim 1, wherein the implantable amplifying circuit has a CMRR higher than 90 dB at 250 Hz.

6. The implantable amplifying circuit of claim 1, wherein the implantable amplifying circuit has a power consumption lower than 12 mW.

7. The implantable amplifying circuit of claim 1, wherein the preamplifier has an input DC current that is lower than 1 nanoamp.

8. The implantable amplifying circuit of claim 1, wherein said implantable amplifying circuit is powered by an RF telemetry link.

9. The implantable amplifying circuit of claim 1, wherein the implantable amplifying circuit has a PSRR higher than 85 dB at 3 kHz.

10. The implantable amplifying circuit of claim 1, wherein said implantable amplifying circuit is powered by a battery.

11. An implantable amplifying circuit for recording electrical signals generated by a nerve and detected by a pair of electrode wires in contact with the nerve, the amplifying circuit comprising:
    a preamplifier having a pair of inputs for receiving signals from the pair of electrode wires, the preamplifier including a differential pair of input MOSFET transistors having a low input current that serves as a first protection circuit to limit current flow through the nerve and the electrode wires;
    a common signal line adapted to connect a body ground of a patient to a common voltage of the amplifying circuit;
    a second protection circuit disposed in series with the common signal line including a parallel resistor/capacitor combination to limit current flow through the nerve and the common signal line;
    at least one amplifier stage connected to an output at the preamplifier that produces an amplified nerve output signal;
    a DC restoration circuit having an input connected to an output of said amplifier stage.

12. An implantable amplifying circuit for recording electrical signals generated by a nerve and detected by a pair of electrode wires in contact with the nerve, the amplifying circuit comprising:
    a preamplifier having a pair of inputs for receiving signals from the pair of electrode wires, the preamplifier including a differential pair of input MOSFET transistors having a low input current that serves as a first protection circuit to limit current flow through the nerve and the electrode wires;
    a common signal line adapted to connect a body ground of a patient to a common voltage of the amplifying circuit;
    a second protection circuit disposed in series with the common signal line including a parallel resistor/capacitor combination to limit current flow through the nerve and the common signal line;
    at least one band-pass amplifier connected to an output at the preamplifier that produces an amplified nerve output signal.

13. The implantable amplifying circuit of claim 12, wherein said band-pass amplifier comprises a plurality of high-pass filters and a plurality of low-pass negative-feed back amplifiers alternatingly cascaded with said high-pass filters.

14. The implantable amplifying circuit of claim 13, wherein each low-pass negative-feedback amplifier comprises:
  a plurality of series-connected resistors forming a resistor string connected between an output terminal and a voltage reference terminal of the low-pass negative-feedback amplifier; and
  a plurality of selectable switches wherein an end of each selectable switch is connected to an input terminal of the low-pass negative-feedback amplifier and another end of each selectable switch is connected to a nodal point between the resistors in the resistor string.

15. The implantable amplifying circuit of claim 13, wherein each low-pass negative-feedback amplifier comprises an output stage in a Darlington configuration operating as a class AB amplifier wherein a bias circuit supplying bias to the output stage also carries signal current.

16. The implantable amplifying circuit of claim 12, wherein said band-pass amplifier is a programmable-gain band-pass amplifier.

17. The implantable amplifying circuit of claim 16, wherein said programmable-gain band-pass amplifier has a frequency range between approximately 900 Hz and 9 kHz for 5 $\mu V_{peak}$ input neural signals.

* * * * *